(12) United States Patent
Ikhlef et al.

(10) Patent No.: US 7,233,640 B2
(45) Date of Patent: Jun. 19, 2007

(54) CT DETECTOR HAVING AN OPTICAL MASK LAYER

(75) Inventors: Abdelaziz Ikhlef, Waukesha, WI (US); Gregory S. Zeman, Waukesha, WI (US); George E. Possin, Niskayuna, NY (US); Li Wen, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 166 days.

(21) Appl. No.: 10/707,407

(22) Filed: Dec. 11, 2003

(65) Prior Publication Data

US 2005/0111612 A1 May 26, 2005

Related U.S. Application Data

(60) Provisional application No. 60/525,377, filed on Nov. 26, 2003.

(51) Int. Cl.
*A61B 6/03* (2006.01)
*G01T 1/20* (2006.01)

(52) U.S. Cl. .................. 378/19; 378/98.8; 250/370.11; 250/368

(58) Field of Classification Search .................. 378/19, 378/154, 98.8; 250/370.11, 366, 367, 368
See application file for complete search history.

(56) References Cited

U.S. PATENT DOCUMENTS

| | | | | |
|---|---|---|---|---|
| 4,948,978 A | * | 8/1990 | Guyot | 250/370.11 |
| 4,982,096 A | * | 1/1991 | Fujii et al. | 250/370.11 |
| 5,430,298 A | * | 7/1995 | Possin et al. | 250/370.09 |
| 5,682,411 A | * | 10/1997 | Rushbrooke et al. | 378/98.8 |
| 6,473,486 B2 | | 10/2002 | Hoffman | |
| 6,480,562 B2 | | 11/2002 | Jiang et al. | |
| 6,480,563 B2 | | 11/2002 | Hoffman et al. | |
| 6,534,773 B1 | * | 3/2003 | Iwanczyk et al. | 250/370.11 |
| 6,553,092 B1 | * | 4/2003 | Mattson et al. | 378/19 |
| 6,654,443 B1 | | 11/2003 | Hoffman | |
| 6,847,701 B2 | * | 1/2005 | Hoheisel et al. | 378/154 |

* cited by examiner

*Primary Examiner*—Edward J. Glick
*Assistant Examiner*—Chih-Cheng Glen Kao
(74) *Attorney, Agent, or Firm*—Ziolkowski Patent Solutions Group, SC

(57) ABSTRACT

An optical mask layer for a CT detector is disclosed and is disposed between the photodiode array and scintillator array of a CT detector. The optical mask layer, which may extend along the x-axis, z-axis, or both, is designed to absorb and/or reflect light emitted the scintillators of the scintillator array. Through this absorption and/or reflection, transference of light photons from a scintillator to the photodiode corresponding to a neighboring scintillator is reduced. This reduction in cross-talk reduces artifacts in a reconstructed image and therefore improves the diagnostic value of the image.

21 Claims, 5 Drawing Sheets

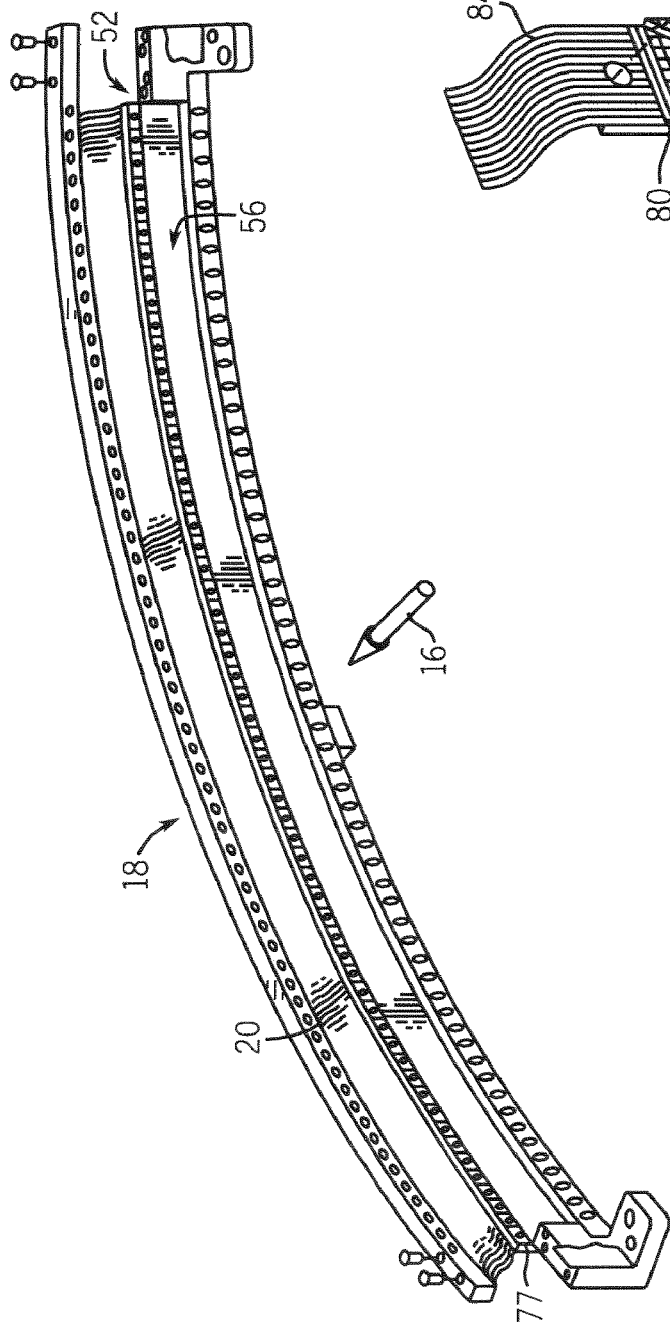
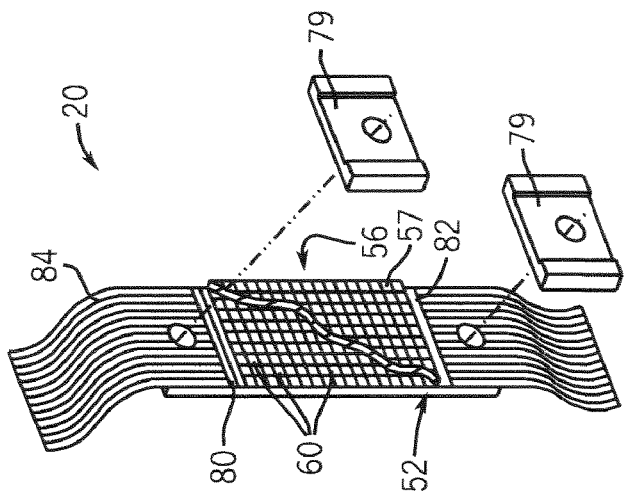
FIG. 3
FIG. 4

CT DETECTOR HAVING AN OPTICAL MASK LAYER

CROSS REFERENCE TO RELATED APPLICATIONS

The present invention claims the benefit of provisional application U.S. Ser. No. 60/525,377, filed Nov. 26, 2003 and titled "Reduction of Cross-talk in CT Detector Using Back Striped 2D Array Photodiodes".

BACKGROUND OF INVENTION

The present invention relates generally to diagnostic imaging and, more particularly, to a CT detector having an optical mask layer to reduce cross-talk between scintillators and neighboring photodiodes.

Typically, in computed tomography (CT) imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom.

Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction.

Generally, the photodiode is used to convert light signal or energy received to an electric current. Typically, the amount or value of the electric current generated is linearly proportional to the amount of light energy or signal detected. In this regard, for efficient and effective image reconstruction, it is imperative that the x-rays received by a scintillator, light emitted by the scintillator, and the light detected by the photodiode be localized. That is, the quality of the output of a photodiode may be compromised if there is a cross-communication between neighboring detector cells. This cross-communication is generally referred to as "cross-talk".

"Cross-talk" between detector cells of a CT detector occurs when data or signal is transferred between neighboring detector cells. Generally, cross-talk is sought to be reduced as cross-talk leads to artifact presence in the final reconstructed CT image and contributes to poor spatial resolution. Typically, four different types of cross-talk may result within a single CT detector. X-ray cross-talk may occur due to x-ray scattering between scintillator cells. Optical reflector cross-talk occurs by transmission of light through the reflectors that surround the scintillators. Known CT detectors utilize a contiguous optical coupling layer(s), typically epoxy, to secure the scintillator array to the photodiode array. This coupling layer produces an optical coupling cross-talk. This is due to light which is trapped and passes through the optical coupling layer into the region above an adjacent diode, where it is finally absorbed in the diode and converted to electrical signal. A fourth type of cross-talk is diffusion cross-talk. It is a combination of electrical and optical. This is due to optical photons which are typically generated close to the boundary between diode regions. The optical generated carriers diffuse within the field free regions of the diode and some are collected by adjacent diodes producing cross-talk. Both optical coupling cross-talk and diffusion cross-talk as defined above will be described as optical transference or optical transference cross-talk.

Cross-talk and especially cross-talk variation is a significant source of artifacts in CT imagers. To reduce cross-talk variation (in any form) between detector cells, the CT detector is manufactured to extremely tight tolerance so that high quality and artifact-free CT images may be reconstructed. Many of the cross-talk mechanism are very sensitive to small variations in detector dimensions and other properties. The misalignment of the scintillator array to the photodiode array drives the non-uniformity of cross-talk level from one cell to its neighbors. In order to reduce the variation of crosstalk from one cell to another, either a better alignment of diode to scintillator or a non-sensitive design is required.

One of the contributors of this cell-to-cell variation of cross-talk is the electrical cross-talk generated by diffusion of photo generated carriers between the individual photodiode elements. The lateral diffusion of photo generated carriers can be thought of as an increase in the photoactive area of the photodiode collection junction. This lateral diffusion leads to a lateral cross-talk which occurs when some photocarriers diffuse out of the cell collection site in which they are generated and are collected by a neighboring cell. This effect is even more pronounced in back-illuminated diodes because the thickness of the diodes increases the diffusion length before collection. A back-illuminated diode is a diode array where the light is incident on the side of the diode array opposite from the diode junctions.

It would therefore be desirable to design a CT detector with reduced electrical cross-talk for improved image reconstruction.

BRIEF DESCRIPTION OF INVENTION

The present invention is directed to a CT detector employing an optical mask to reduce cross-talk and cross-talk variation between photodiodes overcoming the aforementioned drawbacks.

An optical mask layer is disposed or otherwise formed between the photodiode array and scintillator array of a CT detector. The optical mask layer, which may extend along the x-axis, z-axis, or both, is designed to absorb or reflect light emitted by the scintillators of the scintillator array in the regions near the boundaries between photodiodes. Through this absorption or reflection, transference of light photons into electrical signals from a scintillator to the photodiode corresponding to a neighboring scintillator is reduced. The transference which is suppressed may occur by two mechanisms: first, by optical transmission through the optical coupling layer and, second, by generation of electrical carriers in the semiconductor and lateral diffusion of these carriers to an adjacent photodiode. This reduction in cross-talk reduces artifacts in the reconstructed image and therefore improves the diagnostic value of the image. In an alternate embodiment, optically reflective materials rather than or in addition to the optically absorbent materials are used.

Therefore, in accordance with one aspect, the present invention includes a CT detector having a scintillator array that includes a plurality of scintillators and a photodiode array having a plurality of photodiodes and configured to detect illumination of the scintillator array. The CT detector also includes an optical mask disposed between the scintillator array and the photodiode array. The optical mask is configured to reduce optical transference between a scintillator and a neighboring photodiode.

In accordance with another aspect of the present invention, a CT detector is provided and includes at least two scintillators positioned adjacently to one another and at least two photodiodes. Each photodiode is operationally aligned to detect illumination of a respective scintillator. The CT detector further includes at least one mask element disposed between the at least two scintillators and the at least two photodiodes to reduce optical transference between a scintillator and a neighboring photodiode.

According to another aspect, the present invention includes a CT system having a rotatable gantry having a bore centrally disposed therein and a table movable fore and aft through the bore and configured to position a subject for CT data acquisition. The CT system also includes a high frequency electromagnetic energy projection source positioned within the rotatable gantry and configured to project high frequency electromagnetic energy toward the subject, and a detector array disposed within the rotatable gantry and configured to detect high frequency electromagnetic energy projected by the projection source and impinged by the subject. The detector array includes an array of scintillators and an array of photodiodes. The detector array further includes an array of optical cross-talk inhibitors interstitially layered between the array of scintillators and the array of photodiodes.

In accordance with yet another aspect, the present invention includes a method of CT detector manufacture that includes the steps of providing a cellular arrangement of scintillators and providing a cellular arrangement of photodiodes. The manufacturing method further includes providing an optical cross-talk mask and arranging the cellular arrangement of scintillators and the cellular arrangement of photodiodes such that the optical cross-talk mask is sandwiched therebetween.

Various other features, objects and advantages of the present invention will be made apparent from the following detailed description and the drawings.

BRIEF DESCRIPTION OF DRAWINGS

The drawings illustrate one preferred embodiment presently contemplated for carrying out the invention.

In the drawings:

FIG. 3 is a perspective view of one embodiment of a CT system detector array.

FIG. 4 is a perspective view of one embodiment of a detector.

DETAILED DESCRIPTION

The operating environment of the present invention is described with respect to a four-slice computed tomography (CT) system. However, it will be appreciated by those skilled in the art that the present invention is equally applicable for use with single-slice or other multi-slice configurations. Moreover, the present invention will be described with respect to the detection and conversion of x-rays. However, one skilled in the art will further appreciate that the present invention is equally applicable for the detection and conversion of other high frequency electromagnetic energy such as gamma rays or higher energy particle radiation such as neutrons, electrons or protons. The present invention will be described with respect to a "third generation" CT scanner, but is equally applicable with other CT systems.

Figure 1:
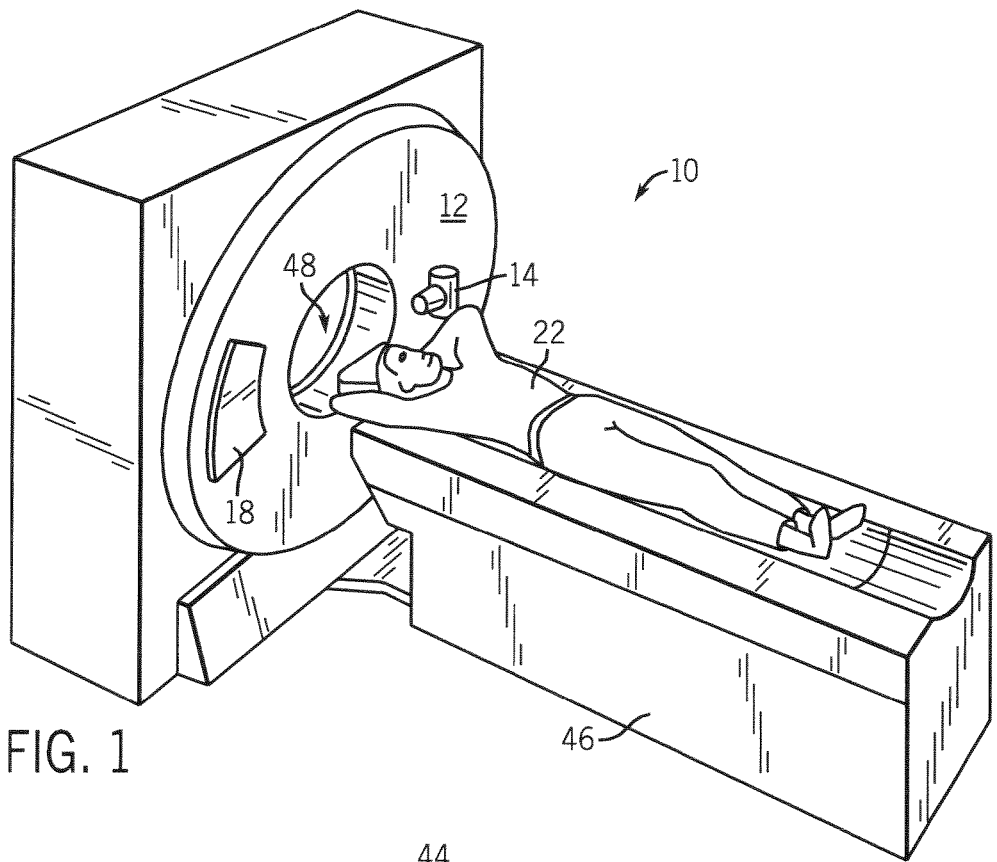
FIG. 1 is a pictorial view of a CT imaging system.
Figure 2:
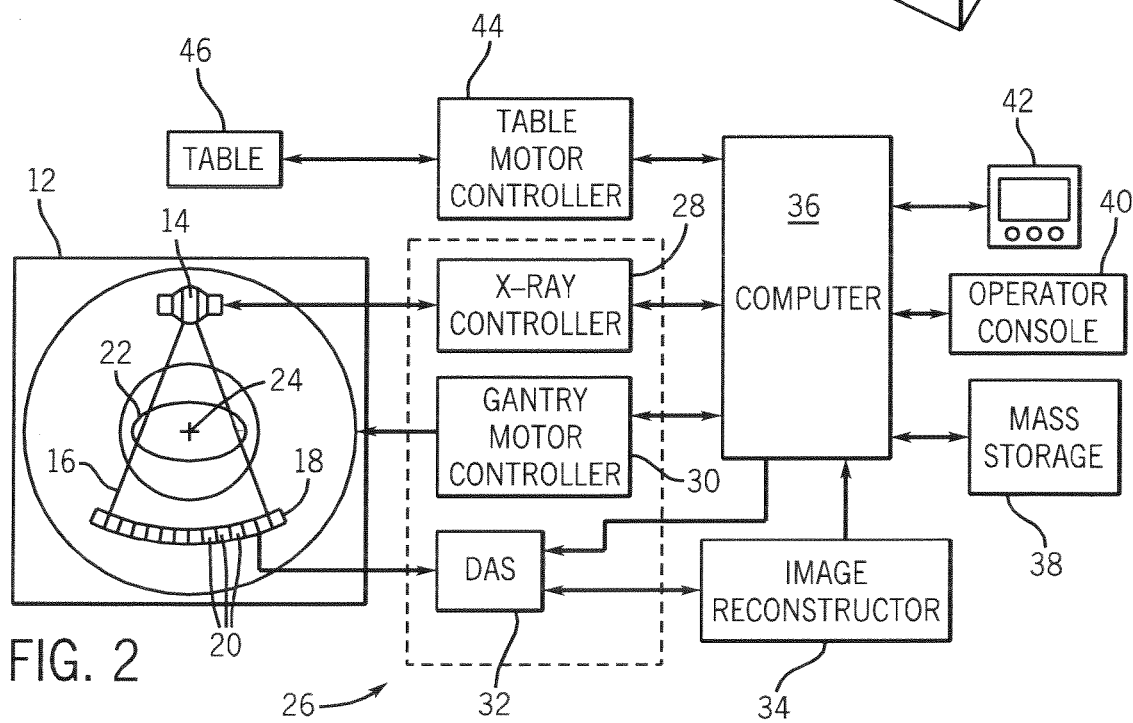
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of the gantry 12. Detector array 18 is formed by a plurality of detectors 20 which together sense the projected x-rays that pass through a medical patient 22. Each detector 20 produces an electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. A data acquisition system (DAS) 32 in control mechanism 26 samples analog data from detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves portions of patient 22 through a gantry opening 48.

As shown in FIGS. 3 and 4, detector array 18 includes a plurality of scintillators 57 forming a scintillator array 56. A collimator (not shown) is positioned above scintillator array 56 to collimate x-ray beams 16 before such beams impinge upon scintillator array 56.

In one embodiment, shown in FIG. 3, detector array 18 includes 57 detectors 20, each detector 20 having an array size of 16×16. As a result, array 18 has 16 rows and 912 columns (16×57 detectors) which allows 16 simultaneous slices of data to be collected with each rotation of gantry 12. Further, as will be described in greater detail below, each detector includes an optical mask or layer designed to reduce cross-talk between detector cells adjacent to one another along the x-axis, between detector cells adjacent to one another along the z-axis, or both. By convention the two in plane axes of the detector are the x-axis and the z-axis. The x-axis is in the direction of the gantry rotation.

Switch arrays 80 and 82, FIG. 4, are multi-dimensional semiconductor arrays coupled between scintillator array 56 and DAS 32. Switch arrays 80 and 82 include a plurality of field effect transistors (FET) (not shown) arranged as multi-dimensional array. The FET array includes a number of electrical leads connected to each of the respective photodiodes 60 and a number of output leads electrically connected to DAS 32 via a flexible electrical interface 84. Particularly, about one-half of photodiode outputs are electrically connected to switch 80 with the other one-half of photodiode outputs electrically connected to switch 82. Additionally, a reflector layer (not shown) may be interposed between each scintillator 57 to reduce light scattering from adjacent scintillators. Each detector 20 is secured to a detector frame 77, FIG. 3, by mounting brackets 79.

Switch arrays 80 and 82 further include a decoder (not shown) that enables, disables, or combines photodiode outputs in accordance with a desired number of slices and slice resolutions for each slice. Decoder, in one embodiment, is a decoder chip or a FET controller as known in the art. Decoder includes a plurality of output and control lines coupled to switch arrays 80 and 82 and DAS 32. In one embodiment defined as a 16 slice mode, decoder enables switch arrays 80 and 82 so that all rows of the photodiode array 52 are activated, resulting in 16 simultaneous slices of data for processing by DAS 32. Of course, many other slice combinations are possible. For example, decoder may also select from other slice modes, including one, two, and four-slice modes.

Figure 5:
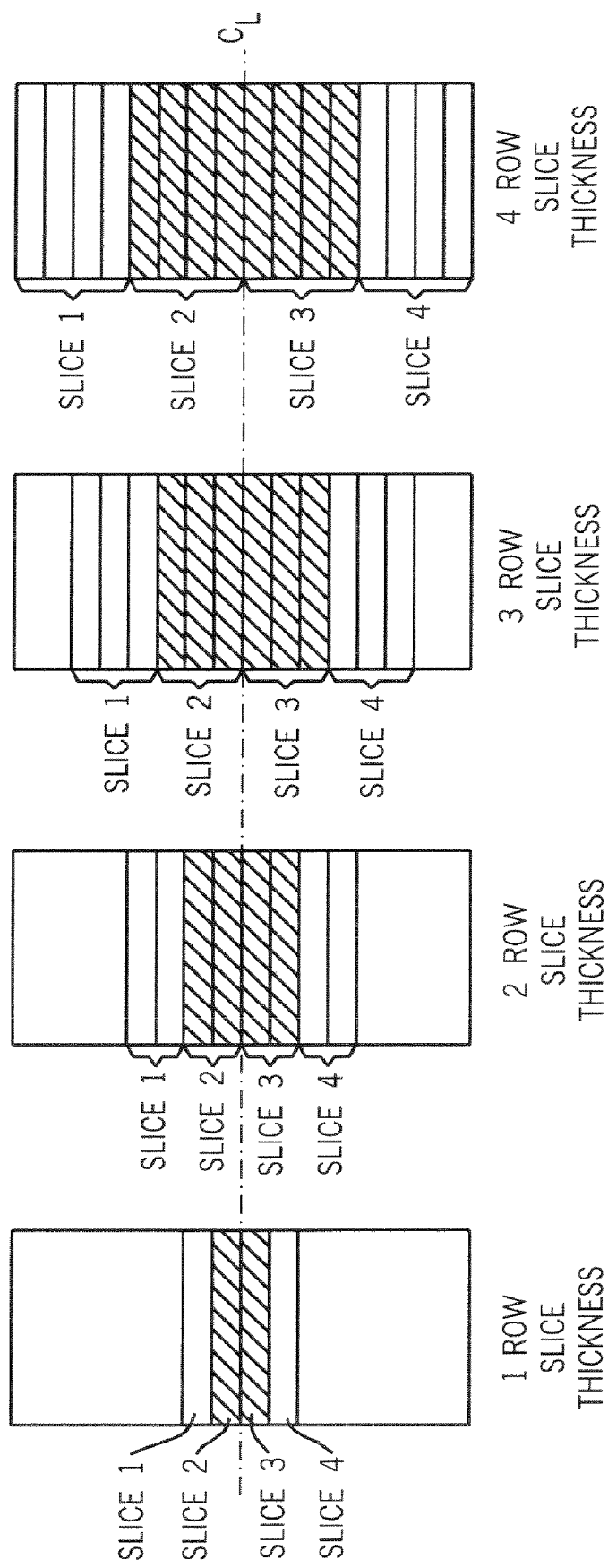
FIG. 5 is illustrative of various configurations of the detector in FIG. 4 in a four-slice mode.

As shown in FIG. 5, by transmitting the appropriate decoder instructions, switch arrays 80 and 82 can be configured in the four-slice mode so that the data is collected from four slices of one or more rows of photodiode array 52. Depending upon the specific configuration of switch arrays 80 and 82, various combinations of photodiodes 60 can be enabled, disabled, or combined so that the slice thickness may consist of one, two, three, or four rows of scintillator array elements 57. Additional examples include, a single slice mode including one slice with slices ranging from 1.25 mm thick to 20 mm thick, and a two slice mode including two slices with slices ranging from 1.25 mm thick to 10 mm thick. Additional modes beyond those described are contemplated.

The present invention is directed to an optical mask or layer constructed to reduce the absorption of photons from the scintillator in the regions near the gaps between detector cells in the diode. Photo generated carriers in the diode in these regions have the highest probability of diffusion and collection by an adjacent detector cell. Specifically, the optical mask forms a grid of intersecting optical absorbing inhibitor elements extending transversely along and dimensionally equivalent to the scintillator array and the photodiode array. Additionally, the mask may be constructed of an optical reflective material(s) rather than or in addition to absorbing material(s) or opaque material(s). More specifically, the mask may be preferably constructed of any one or combination of black polyamide, metal, doped silicon, and opaque material(s).

Figure 6:
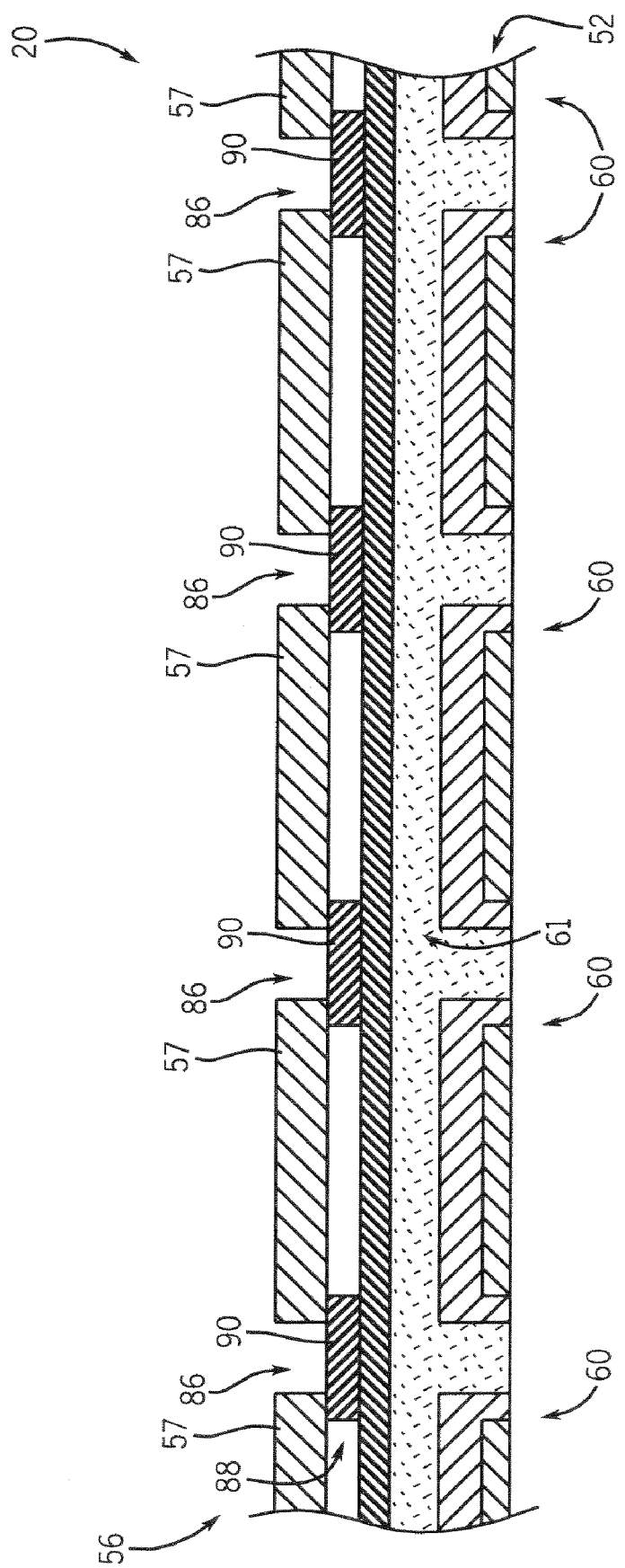
FIG. 6 is cross-sectional view of a portion of a CT detector in accordance with one aspect of the present invention.

FIG. 6 illustrates a cross-sectional view of a portion of a CT detector 20 in accordance with the present invention. As illustrated and described above, detector 20 includes a scintillator array 56 formed of a plurality of scintillators 57. Neighboring scintillators are separated from one another by a gap 86 that is typically filled with optically reflective material to form a reflector. Optically coupled to the scintillator array 56 is a photodiode array 52 comprised of photodiodes 60 fabricated in a semiconductor substrate 61. Each scintillator 57 has a corresponding photodiode 60. Sandwiched between the scintillator array and the substrate is an optical mask or layer 88 that includes a number of mask elements 90. As noted above, the optical mask may be constructed such that the mask elements extend along the x-axis, z-axis, or both.

The optical absorbing mask 88 is designed to reduce cross-talk from one detector cell to its neighbor. More specifically, the optical mask elements 90 are designed to reduce cross-talk from a scintillator and the photodiode of a neighboring scintillator. Moreover, the optical mask is designed to accommodate the misalignment of detector components and the cross-talk associated therewith. That is, the optical mask is constructed such that the individual mask elements are dimensionally equivalent to, and preferably larger than, the separation between adjacent scintillators. As such, the optical mask may be used to relax the alignment requirements of the scintillator array to the photodiode array. The region of optical photon absorption in the diode is defined by the placement of the mask 88 and not the alignment of the scintillator array 56. In addition, it is preferred that the thickness of the optical mask elements be substantially equivalent to the vertical separation between the scintillator array and the photodiode array.

It is contemplated that the optical mask may be comprised of a number of optically absorbing materials and may be manufactured in accordance with a number of fabrication techniques. In this regard, black polyamide is one example of a composition that may be used in the optical absorption layer. Such black polyamide materials are commercially available from Brewer Science, Inc. of Rolla, Mo. Moreover, metal and a metallization fabrication process are contemplated. In another embodiment, the photodiode array may be deposited or otherwise diffused with a dopant which produces rapid recombination of the photogenerated carriers. An example is a high concentration of N type dopant, if the diodes are formed from P-type dopant. In another embodiment, a mechanical grid dimensionally equivalent to the photodiode array is fabricated and applied. Screen printing of opaque materials is also contemplated for optical mask construction. Additionally, heretofore the present invention has been described with respect to the reduction of cross-talk between a scintillator and a neighboring photodiode through incorporation of an optically absorbent element between photodiodes; however, it is contemplated that the light photons emitted toward a neighboring detector cell may be blocked and/or reflected using optically reflective elements. In this regard, light collection may be increased with a reduction of cross-talk. It is also contemplated that angled reflective elements may be used to further enhance light collection efficiency.

Figure 7:
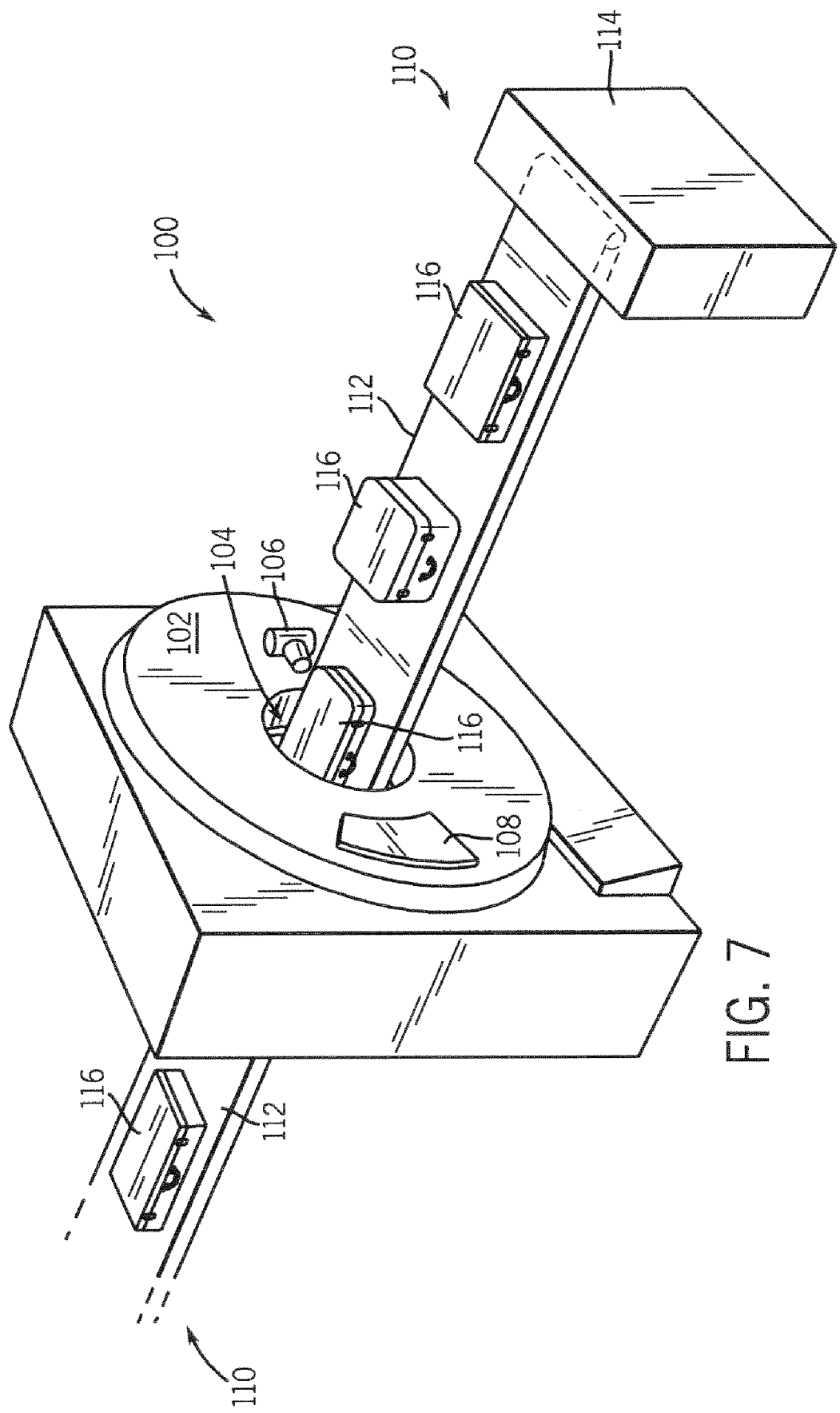
FIG. 7 is a pictorial view of a CT system for use with a non-invasive package inspection system.

The present invention has been described with respect to the acquisition of diagnostic data from a medical patient. The present invention is also applicable with CT systems used to acquire non-medical data. Referring now to FIG. 7, package/baggage inspection system 100 includes a rotatable gantry 102 having an opening 104 therein through which packages or pieces of baggage may pass. The rotatable gantry 102 houses a high frequency electromagnetic energy source 106 as well as a detector assembly 108 having scintillator arrays comprised of scintillator cells. A conveyor system 110 is also provided and includes a conveyor belt 112 supported by structure 114 to automatically and continuously pass packages or baggage pieces 116 through opening 104 to be scanned. Objects 116 are fed through opening 104 by conveyor belt 112, imaging data is then acquired, and the conveyor belt 112 removes the packages 116 from opening 104 in a controlled and continuous manner. As a result, postal inspectors, baggage handlers, and other security personnel may non-invasively inspect the contents of packages 116 for explosives, knives, guns, contraband, etc.

Therefore, in accordance with one embodiment, the present invention includes a CT detector having a scintillator array that includes a plurality of scintillators and a photodiode array having a plurality of photodiodes and configured to detect illumination of the scintillator array. The CT detector also includes an optical mask disposed between the scintillator array and the photodiode array. The optical mask is configured to reduce optical transference between a scintillator and a neighboring photodiode.

In accordance with another embodiment of the present invention, a CT detector is provided and includes at least two scintillators positioned adjacently to one another and at least two photodiodes. Each photodiode is operationally aligned to detect illumination of a respective scintillator. The CT detector further includes at least one mask element disposed between the at least two scintillators and the at least two photodiodes to reduce optical transference between a scintillator and a neighboring photodiode.

According to another embodiment, the present invention includes a CT system having a rotatable gantry having a bore centrally disposed therein and a table movable fore and aft through the bore and configured to position a subject for CT data acquisition. The CT system also includes a high frequency electromagnetic energy projection source positioned within the rotatable gantry and configured to project high frequency electromagnetic energy toward the subject, and a detector array disposed within the rotatable gantry and configured to detect high frequency electromagnetic energy projected by the projection source and impinged by the subject. The detector array includes an array of scintillators and an array of photodiodes. The detector array further includes an array of optical cross-talk inhibitors interstitially layered between the array of scintillators and the array of photodiodes.

In accordance with yet another embodiment, the present invention includes a method of CT detector manufacture that includes the steps of providing a cellular arrangement of scintillators and providing a cellular arrangement of photodiodes. The manufacturing method further includes providing an optical cross-talk mask and arranging the cellular arrangement of scintillators and the cellular arrangement of photodiodes such that the optical cross-talk mask is sandwiched therebetween.

The present invention has been described in terms of the preferred embodiment, and it is recognized that equivalents, alternatives, and modifications, aside from those expressly stated, are possible and within the scope of the appending claims.

What is claimed is:

1. A CT detector comprising:
   a scintillator array having a plurality of scintillators arranged along a first plane;
   a photodiode array having a plurality of photodiodes arranged along a second plane different from the first plane and parallel to the first plane, and configured to detect illumination of the scintillator array;
   the first plane and the second plane orthogonal to a direction of x-ray incidence on the scintillator array; and
   an optical mask formed of optical absorbing material and arranged and extended in major part along a third plane parallel to the first and the second planes, and disposed between the scintillator array and the photodiode array without encroachment upon any of the first plane or the second plane, the optical mask configured to reduce optical transference between a scintillator and a neighboring photodiode, the optical mask located closer to the scintillator array than the plurality of photodiodes.

2. The CT detector of claim 1 wherein the optical mask includes a grid of intersecting optical inhibitor elements.

3. The CT detector of claim 2 wherein the grid is dimensionally equivalent to the scintillator array and the photodiode array.

4. The CT detector of claim 1 wherein the optical mask is defined by a plurality of parallel optical inhibitor elements extending transversely along a width of the photodiode array.

5. The CT detector of claim 1 wherein each scintillator/photodiode combination defines a detector cell and wherein the optical mask is configured to reduce cross-talk between adjacent cells.

6. The CT detector of claim 1 wherein at least a majority of the optical mask is disposed adjacent to the scintillator array.

7. A CT system comprising:
   a rotatable gantry having a bore centrally disposed therein;
   a table movable fore and aft through the bore and configured to position a subject for CT data acquisition;
   a high frequency electromagnetic energy projection source positioned within the rotatable gantry and configured to project a high frequency electromagnetic energy fan beam toward the subject; and
   a detector array disposed within the rotatable gantry and configured to detect high frequency electromagnetic energy projected by the projection source and impinged by the subject, the detector array including:
   an array of scintillators located in a layer;
   an array of photodiodes located in a layer; and
   an array of optical cross-talk inhibitors formed of optically absorbent material and interstitially layered between, without encroachment upon, the layer of the array of scintillators and the layer of the array of photodiodes, the array of optical cross-talk inhibitors located closer to the layer of the array of scintillators than the array of photodiodes, the array of optical cross-talk inhibitors located in a layer that comprises a substantially same major orientation as the layer of the array of scintillators and the layer of the array of photodiodes.

8. The CT system of claim 7 wherein the array of optical cross-talk inhibitors is fabricated from light absorbent silicon.

9. The CT system of claim 7 wherein the array of optical cross-talk inhibitors is fabricated from opaque materials.

10. The CT system of claim 7 wherein at least a majority of the array of optical cross-talk inhibitors is disposed adjacent to the array of scintillators.

11. A method of CT detector manufacture comprising the steps of:
providing a cellular arrangement of scintillators;
providing a cellular arrangement of photodiodes, each photodiode configured to detect illumination of a corresponding scintillator;
providing an optical cross-talk mask, wherein providing an optical cross-talk mask includes the step of forming a grid of light-absorbing elements; and
arranging the cellular arrangement of scintillators, the cellular arrangement of photodiodes, and the optical cross-talk mask in a multi-planar stack wherein each of the cellular arrangements and the optical cross-talk mask are arranged orthogonal to a central axis of x-ray incidence on the cellular arrangement of scintillators such that the optical cross-talk mask is sandwiched between the cellular arrangement of scintillators and the cellular arrangement of photodiodes, such that the optical cross-talk mask is located closer to the cellular arrangement of scintillators than the cellular arrangement of photodiodes, and such that in the multi-planar stack a plane of the cellular arrangement of scintillators, a plane of the cellular arrangement of photodiodes, and a plane of the optical cross-talk mask comprise a substantially same major orientation.

12. The method of claim 11 wherein the optical cross-talk mask includes a cellular arrangement of mask elements.

13. The method of claim 11 wherein the optical cross-talk mask is formed of one of:
black polyamide;
metal;
doped silicon; and
opaque material(s).

14. The method of claim 11 wherein the optical cross-talk mask is constructed to reduce cross-talk between a scintillator and a neighboring photodiode.

15. The method of claim 11 wherein the step of arranging includes the step of arranging the cellular arrangement of scintillators, the cellular arrangement of photodiodes, and the optical cross-talk mask in the multi-planar stack such that each of the cellular arrangements and the optical cross-talk mask are arranged orthogonal to the central axis of x-ray incidence on the cellular arrangement of scintillators such that at least a majority of the optical cross-talk mask is disposed adjacent to the cellular arrangement of scintillators.

16. A CT detector comprising:
a first scintillator and a second scintillator positioned adjacently to one another and distanced from one another by a given width;
a first photodiode operationally aligned to detect illumination of the first scintillator and a second photodiode operationally aligned to detect illumination of the second scintillator;
at least one mask element of optically absorbing material arranged and extended in major part along a plane disposed between the first and the second scintillators and the first and the second photodiodes to reduce optical transference between the first scintillator and the second photodiode and the second scintillator and the first photodiode, the at least one mask element having a width that exceeds the given width separating the first and the second scintillators from one another, wherein the plane avoids intersection with any of the first scintillator, the second scintillator, the first photodiode, or the second photodiode, the at least one mask element located closer to the first and the second scintillators than the first and the second photodiodes;
wherein the plane comprises a third plane, wherein the first and the second scintillators are arranged along a first plane, wherein the first and the second photodiodes are arranged along a second plane different from the first plane and parallel to the first plane, wherein the first plane and the second plane are orthogonal to a direction of x-ray incidence on the first and the second scintillators, wherein the third plane is parallel to the first and the second planes; and
wherein the at least one mask element of optically absorbing material is arranged and extended in major part along the third plane parallel to the first and the second planes to reduce optical transference between the first scintillator and the second photodiode and the second scintillator and the first photodiode, and disposed between the first and the second scintillators and the first and the second photodiodes without encroachment upon any of the first plane or the second plane.

17. The CT detector of claim 16 wherein the first and the second scintillators are spaced from one another by a lateral gap.

18. The CT detector of claim 16 wherein each scintillator is spaced from its corresponding photodiode by a vertical gap.

19. The CT detector of claim 16 wherein each mask element has a thickness at least equal to a height of the vertical gap.

20. The CT detector of claim 16 wherein the at least one mask element is fabricated of at least black polyamide.

21. The CT detector of claim 16 wherein a portion of the mask element is disposed adjacent to the first and second scintillators.

* * * * *